US009563948B2

(12) United States Patent
Piper

(10) Patent No.: US 9,563,948 B2
(45) Date of Patent: Feb. 7, 2017

(54) SYSTEM AND METHOD OF APPLYING AN ARBITRARY ANGLE TO REFORMAT MEDICAL IMAGES

(71) Applicant: MIM Software Inc., Cleveland, OH (US)

(72) Inventor: Jonathan William Piper, Cleveland Heights, OH (US)

(73) Assignee: MIM SOFTWARE, INC., Cleveland, OH (US)

( * ) Notice: Subject to any disclaimer, the term of this patent is extended or adjusted under 35 U.S.C. 154(b) by 227 days.

(21) Appl. No.: 14/564,490

(22) Filed: Dec. 9, 2014

(65) Prior Publication Data

US 2015/0093012 A1   Apr. 2, 2015

Related U.S. Application Data

(63) Continuation of application No. 13/097,356, filed on Apr. 29, 2011, now Pat. No. 8,908,940.

(60) Provisional application No. 61/329,442, filed on Apr. 29, 2010.

(51) Int. Cl.
| G06K 9/00 | (2006.01) |
| G06T 7/00 | (2006.01) |
| G06F 17/30 | (2006.01) |
| G06T 3/60 | (2006.01) |
| G06T 15/08 | (2011.01) |

(52) U.S. Cl.
CPC ....... *G06T 7/0012* (2013.01); *G06F 17/30244* (2013.01); *G06T 3/60* (2013.01); *G06T 15/08* (2013.01)

(58) Field of Classification Search
None
See application file for complete search history.

(56) References Cited

U.S. PATENT DOCUMENTS

| 2004/0092786 | A1 | 5/2004 | Zaider et al. |
| 2005/0084178 | A1 | 4/2005 | Lure et al. |
| 2007/0078306 | A1* | 4/2007 | Allison ................ A61N 5/103 600/300 |
| 2007/0167762 | A1 | 7/2007 | Kim et al. |
| 2010/0053208 | A1 | 3/2010 | Menningen et al. |
| 2010/0310144 | A1* | 12/2010 | Chen ................ G06T 11/006 382/131 |
| 2011/0107270 | A1 | 5/2011 | Wang et al. |

\* cited by examiner

*Primary Examiner* — Weiwen Yang
(74) *Attorney, Agent, or Firm* — Tucker Ellis LLP; Evan Perry

(57) ABSTRACT

In accordance with the teachings described herein, systems and methods are provided for generating a seed plan for use in radiation therapy. The system includes an image database, the image database comprising image slices and a seed template database comprising seed templates. A contour engine is configured to generate target contour data to identify one or more objects within each image slice. A reslicer engine is configured to rotate the contoured image about an angle of rotation to produce a resliced contoured image, such that the resliced contoured image is resampled at an angle perpendicular to the angle of rotation and intersecting an isocenter. The system also includes a seed grid engine configured to generate a seed grid perpendicular to the angle of rotation.

23 Claims, 15 Drawing Sheets

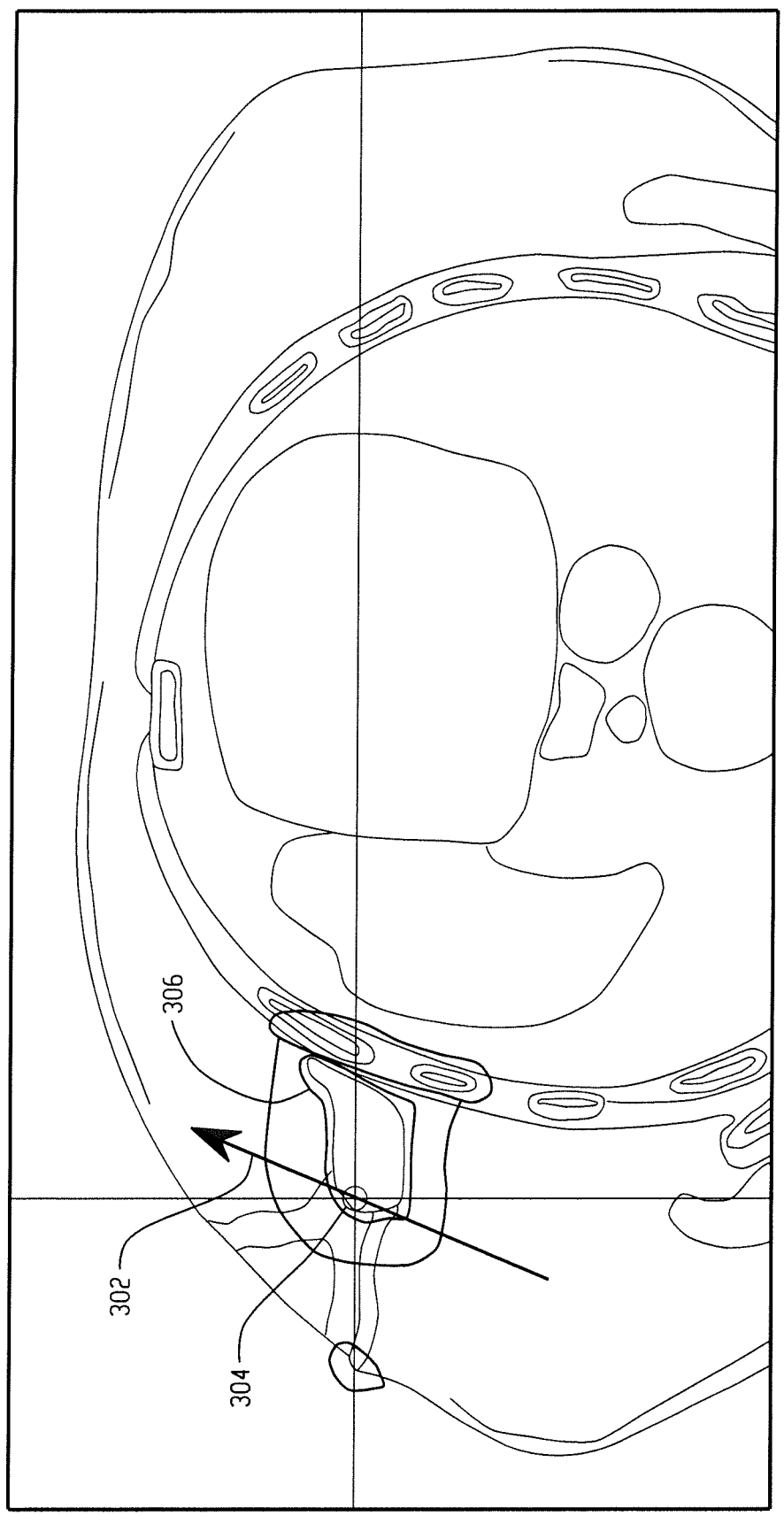

SYSTEM AND METHOD OF APPLYING AN ARBITRARY ANGLE TO REFORMAT MEDICAL IMAGES

CROSS-REFERENCE TO RELATED APPLICATIONS

This application is a continuation of U.S. patent application Ser. No. 13/097,356, filed Apr. 29, 2011, entitled "SYSTEM AND METHOD OF APPLYING AN ARBITRARY ANGLE TO REFORMAT MEDICAL IMAGES". Application Ser. No. 13/097,356 claims priority from U.S. Provisional Patent Application Ser. No. 61/329,442, filed on Apr. 29, 2010. The entireties of the aforementioned applications are incorporated herein by reference.

BACKGROUND

1. Field of the Invention

The technology described in this patent document relates generally to the field of reformatting contoured medical images.

2. Description of Related Art

Contouring is the process of identifying an object within an image by outlining or otherwise distinguishing the object from the rest of the image. Medical images, such as CT (computed tomography), MR (magnetic resonance), US (ultrasound), or PET (positron emission tomography) scans, are regularly contoured to identify certain pieces of anatomy within the image. For example, a radiologist or oncologist may contour a medical image to identify a tumor within the image. Software tools are available to assist in this type of "manual" contouring, in which the physician uses the software to create the contour by tracing the boundary of the object or objects within the image.

Three-dimensional scans, such as CT, MRI, and PET scans, produce a series of two-dimensional (2D) image slices that together make up the 3D image. Contouring these types of 3D images typically requires individually contouring each of the 2D images slices, which can be a laborious process. Systems and methods for contouring 3D images are disclosed in U.S. patent application Ser. No. 12/772,377, filed on May 3, 2010 and titled "Systems and Methods for Contouring a Set of Medical Images," and U.S. patent application Ser. No. 12/772,383, filed on May 3, 2010 and titled "Systems and Methods for Generating a Contour for Medical Image," which are incorporated herein by reference.

Contoured image slices are used in radiation therapy procedures to aid a medical practitioner in the planning of radiation delivery, such as the placement of radiation containing seeds. The, contoured areas provide a target for the placement of seeds, however, the medical practitioner may wish to conduct such a procedure at an angle different than the original contoured image slices.

Re-slicing is generally directed to applying an arbitrary angle to rotate and reformat medical images. The angle may include a user-defined angle for reformatting images to be orthogonal to a planned brachytherapy seed planning path or in plane with an external beam entry path. Re-slicing a contoured image involves manipulating both the original image slices and the contoured image slices. There exists a need to reformat image slices in an efficient manner that allows contoured image data to translate to the reformatted image slices and treatment planning to be performed on the reformatted image slices.

SUMMARY

In accordance with the teachings described herein, systems and methods are provided for generating images and treatment plans for use in radiation therapy. In one example, the system may include an image database, the image database comprising image slices and a seed template database comprising seed templates. A contour engine may be configured to generate target contour data to identify one or more objects within each image slice. A reslicer engine may be configured to rotate the contoured image about an angle of rotation to produce a resliced contoured image, such that the resliced contoured image is resampled at an angle perpendicular to the angle of rotation and intersecting an isocenter. The system may also include a seed grid engine configured to generate a seed grid perpendicular to the angle of rotation.

In one example, a processor-implemented method for reformatting medical image slices may include the steps of receiving one or more image slices, the image slices comprising one or more cross sectional medical images; contouring each image slice to generate target contour data to identify one or more objects within each image slice; defining an isocenter and a needle angle of the image slices, the isocenter defining a center point of a target mass and the needle angle defining the angle of entry for a set of needles; and rotating the contoured image slices about the needle angle to produce a resliced contoured image, the resliced contoured image being the image slice rotated at an angle perpendicular to the needle angle.

DETAILED DESCRIPTION

Figure 1:
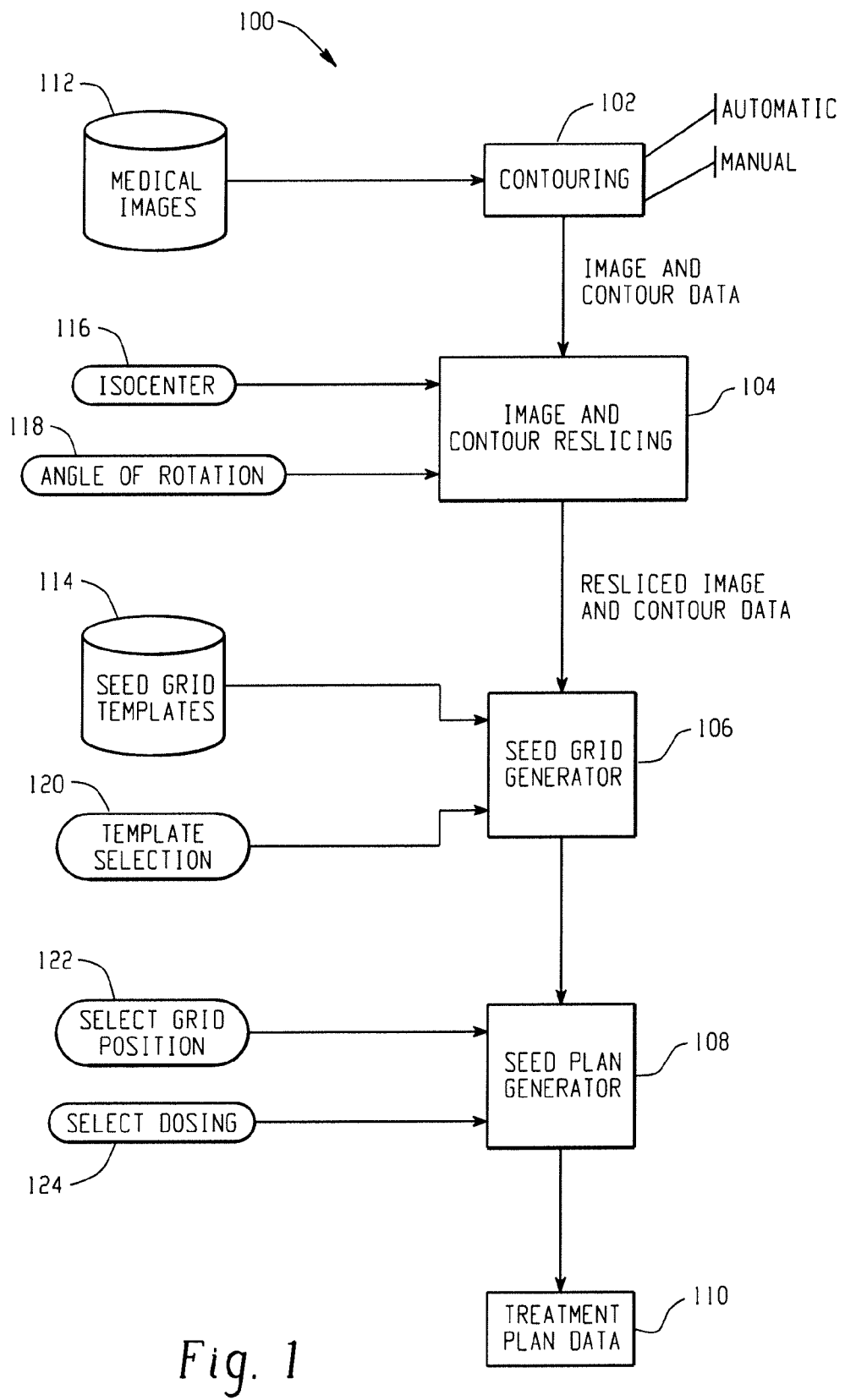
FIGS. 1 and 6 depict block diagrams of example systems for reslicing a set of medical images.

FIG. 1 depicts a block diagram of an example system 100 for reslicing a set of medical images to generate a treatment plan. The system 100 uses medical image data and applies contours to locate a target mass area and a treatment area. The contoured image data is then resliced, or rotated, along a defined needle path or angle of rotation. The rotated image provides a medical practitioner with a needle's eye view of a radiation treatment procedure. In this view, a seed grid is overlaid on the resliced image, allowing the medical practitioner to develop a treatment plan with seed therapy or external beam radiation therapy. As part of the process, the system 100 may produce a treatment plan that details the contoured areas, seed or beam locations and strengths, dosage levels for treatment, and effectiveness of the proposed plan.

The system 100 includes a contouring block 102, an image and contour reslicing block 104, a seed grid generator 106, a seed plan generator 108, and a treatment data plan 110. Also included in the example system 100 are a medical image database 112 for storing a set of two-dimensional image slices, a seed grid template database 114 for storing seed' grid template data, and inputs 116-124. It should be understood that contouring block 102, image and contour reslicing block 104, seed grid generator 106, and seed plan generator 108, as described herein, may be implemented by software instructions executing on one or more processing devices. In other implementations, however, one or more operations of these software engines may instead be performed by other known mechanisms such as firmware or even appropriately designed hardware. The medical image database and seed grid template database, as described herein, may be implemented using one or more memory devices. For instance, in one example the medical image database and seed grid template database may be implemented within the same memory device, and in another example they may be implanted on separate memory devices.

The plurality of medical images are loaded into the medical images database 112 for contouring. The plurality of medical images may include a set of two-dimensional (2D) slices that are received, for example, from a CT scanner or other system for capturing three-dimensional (3D) medical images, such that the set of 2D slices together represent a 3D medical image. In other examples, the plurality of medical image slices could be virtual, such as sagittal or coronal images (or any other slicing angle through the image data).

Figure 2:
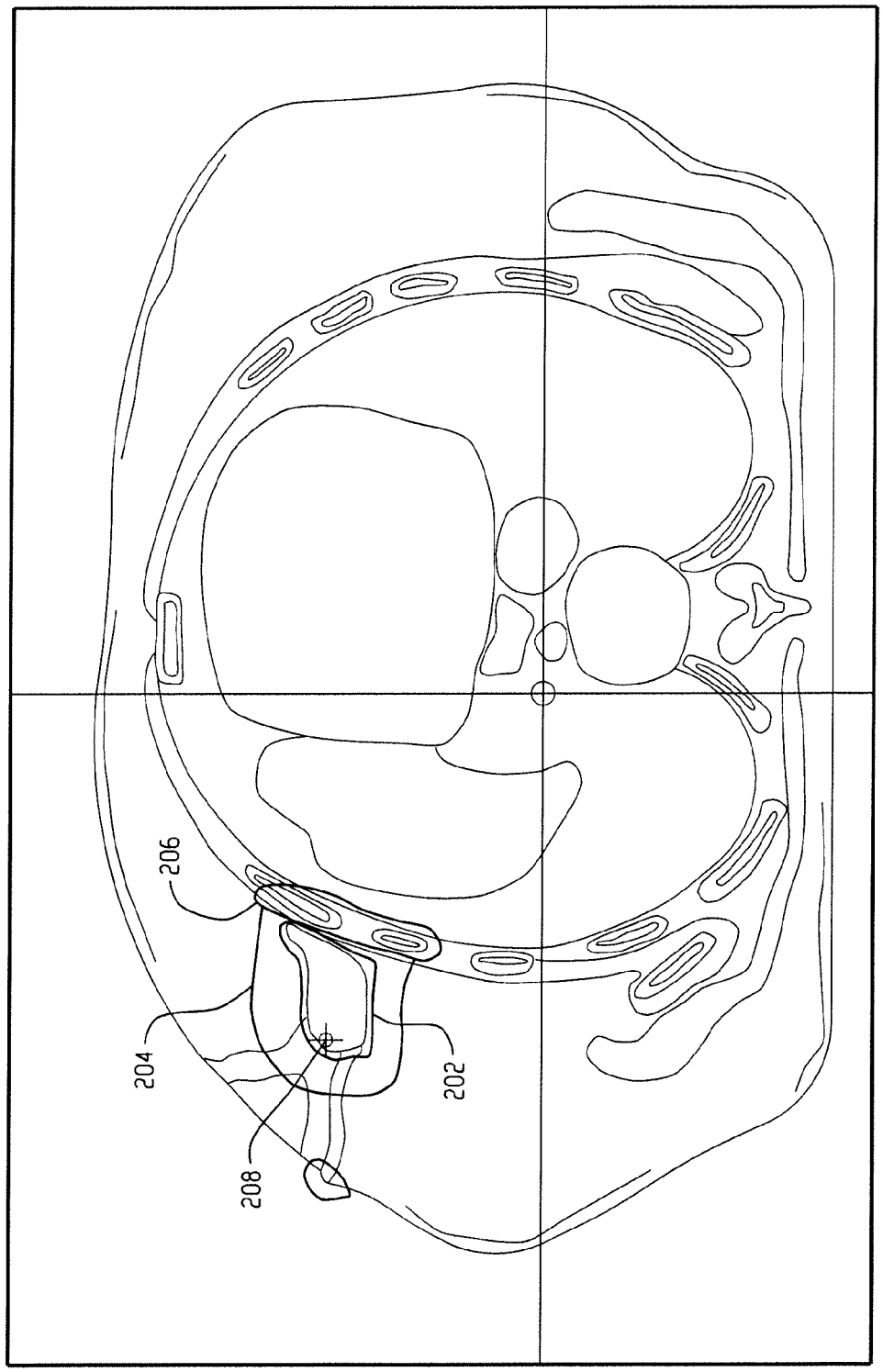
FIGS. 2-5 illustrate examples of contours and resliced images that may be generated by the systems and methods described herein.

In operation, the system 100 receives image slices from the medical images database 112 at the contouring block 102. At the contouring block 102, image slices from the medical images database 112 are contoured according to a contour transformation engine. In one example, the contouring block 102 illustrated in FIG. 1 could be used as a semi-automatic contouring tool that receives initial contour data for one of the image slices and then automatically contours the remaining images slices in the set. In this example, the contouring block 102 may receive contour data for the initial source image from an external source. For instance, the initial contour data may be provided by manually contouring one of the image slices 108 using one of a variety of know manual contouring software applications. Based on the contouring of the initial image slice, the contouring block 102 may automatically contour the remaining image slices based on the contour data from the initial image slice. As shown in FIG. 2, the contouring data may include a clinical target volume contour 202, a planning target volume contour 204, and a chest wall contour 206.

Referring again to FIG. 1, the image and contour reslicing block 104 receives image and contour data from the contouring block 102. With this data, the image and contour reslicing block 104 may define an isocenter 116 and angle of rotation 118. As shown in FIG. 2, a target mass contour 202 is typically applied by the contouring block. The isocenter 208 defines the center point of the treatment volume.

The isocenter may also be utilized to define the angle for rotation 302 of the image. With reference to FIG. 3A, the angle of rotation 302 is typically aligned to intersect with the isocenter. An isocenter 304 is selected at the center of the target mass 304, and the angle of rotation 302 intersects with the isocenter 304, so that the image and contour reslicing block may rotate the image with respect to the proper area of the original medical image. The rotated image provides a rotated viewpoint of the original image slices along the angle of rotation 302. For example, the angle of rotation 302 may coincide with the intended needle path for a radiation therapy procedure.

In order to rotate and reslice the image slices, the image and contour reslicing block 104 formulates the image slices as a 3D image cube. The image and contour reslicing block 104 utilizes the angle of rotation 302 to build a transformation matrix to apply to the image. The transformation matrix is applied to the image cube voxel co-ordinates to generate a new set of voxel co-ordinates which correspond to the voxel positions in the new re-sliced and re-oriented image. The original image slices are then interpolated at the new voxel coordinates to generate the resliced image. The resliced image is sampled into a specified voxel size and image volume dimensions.

To utilize the contours applied in the contouring block 102, the image and contour reslicing block 104 also reslices and reorients any contours associated with the original image slices to the same space as the resliced image slices. The contours are formulated as either a set of 3D mesh objects with boundaries in voxel coordinates into the original image space or as a 3D byte cube with each contour represented as a bitmask with a nonzero bit value for voxels included in each contour and a 0 value where no contour is present. In the first formulation as 3D meshes, the positions can be calculated using the same transformation matrix and transposition scheme as was used for the image. In the second formulation, the bitmask contour is interpolated into a floating point in the same positions as the image cube, and the resulting values thresholded to determine inclusion into a new bitmask contour in the new resliced, reoriented image slice. The threshold may be determined in order to maintain the contour volume or to minimize shifts in contour centriod.

Figure 3B:
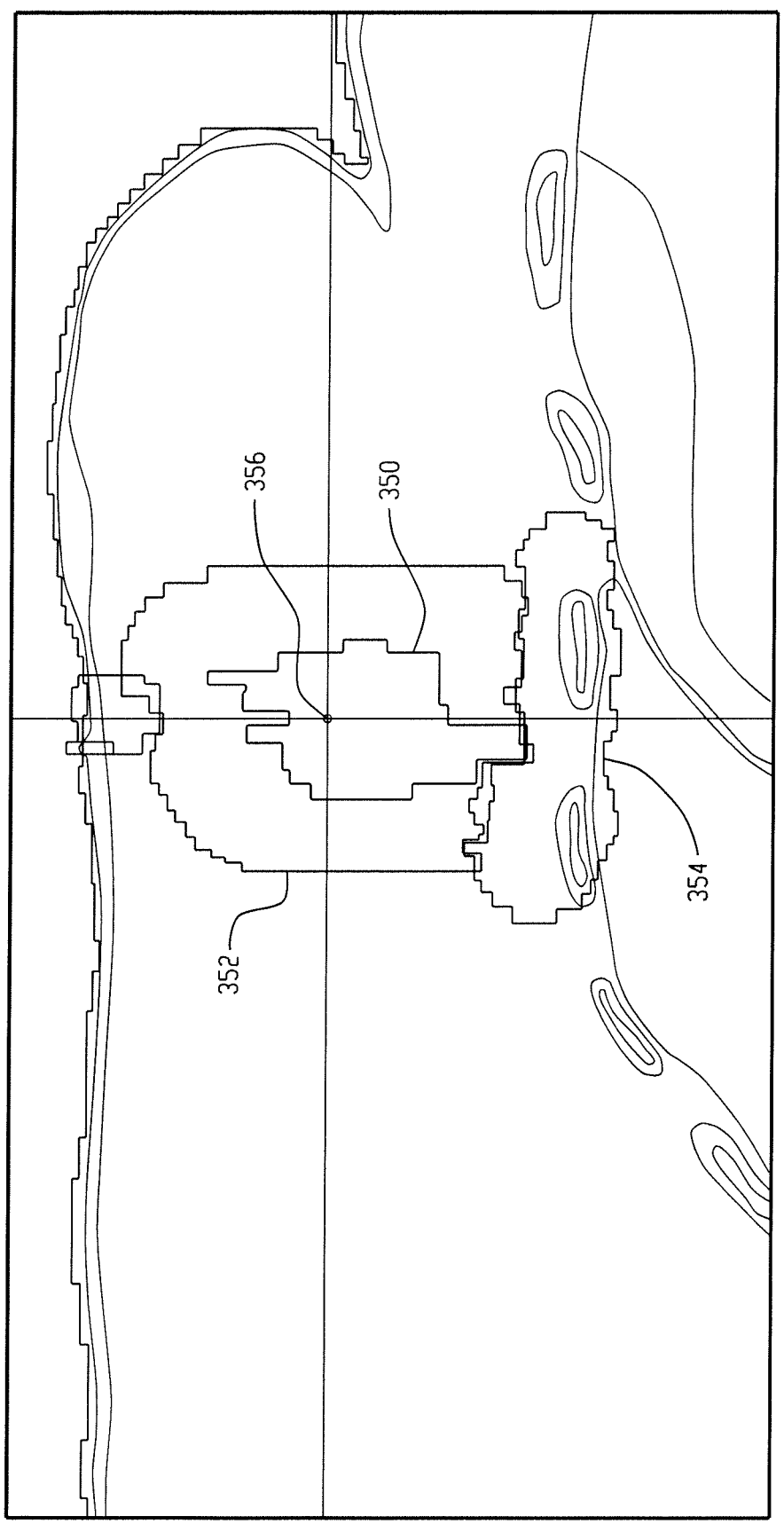

As shown in FIG. 3B, the rotated image slices, provide a viewpoint similar to the actual radiation therapy procedure. From this angle, the same contours from FIG. 3A are represented, but at a different angle than the CT scan image slices. For example, in FIG. 3B, a clinical target volume contour 350, a planning target volume contour 352, and a chest wall contour 354 are each illustrated. Further illustrated in FIG. 3B is the isocenter 356. The isocenter 356 also represents the entry point and needle path or the point at which all external treatment beams intersect for a radiation treatment procedure.

With reference again to FIG. 1, the image and contour reslicing block 104 generates resliced image and contour data, which is received by the seed grid generator 106. At the seed grid generator 106, seed grid template data is received from the seed grid template database 114 along with an input for selecting one or more of the seed grid templates from the seed grid template database 114. The seed grid template database 114 includes seed grid templates that may be used to create a seed grid 402 on the resliced image, as shown in FIG. 4.

Figure 4:
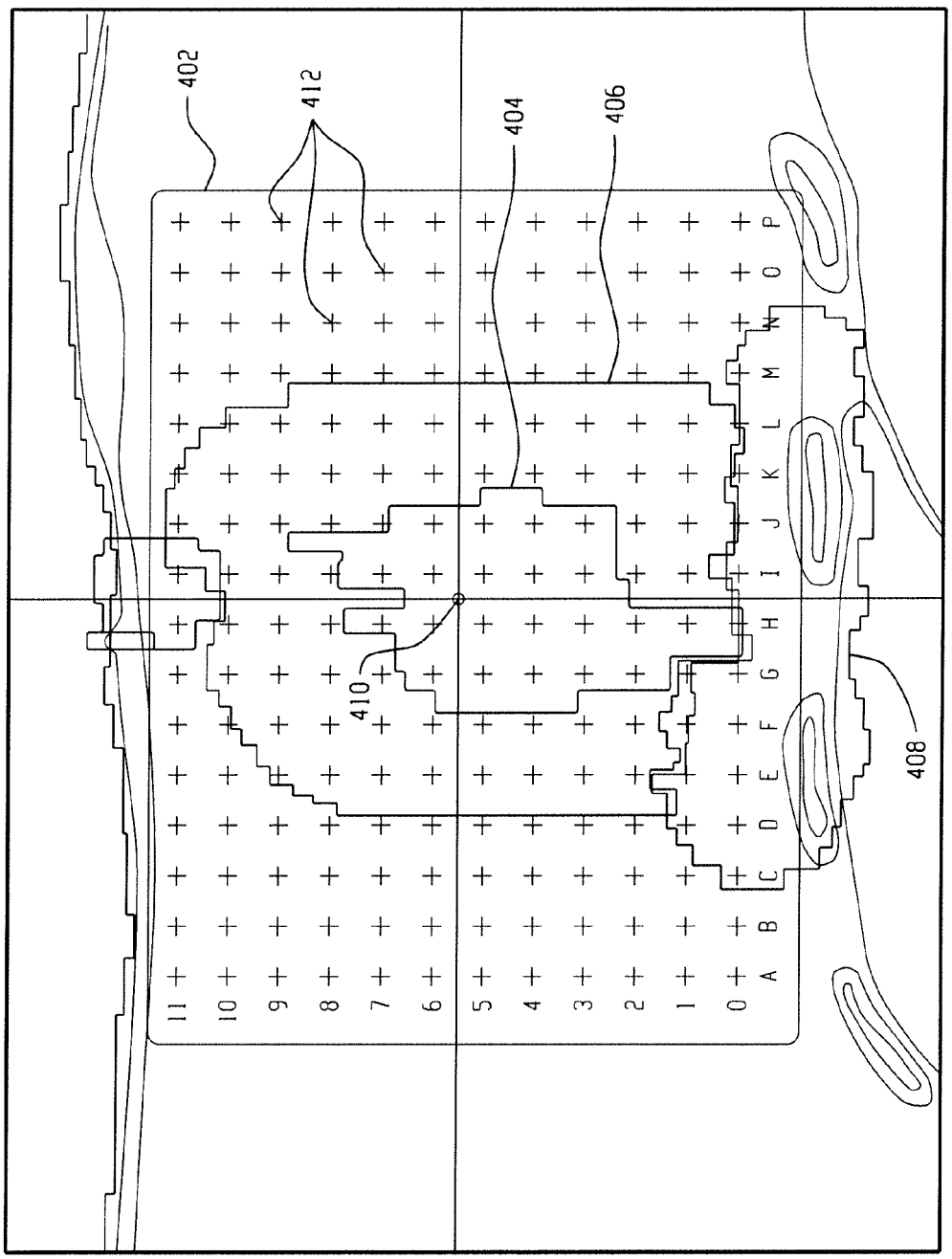

FIG. 4 illustrates a seed grid 402 overlaid on a resliced contoured image slice, such as the example from FIG. 3B. The image contour slices portrayed in FIG. 3B are also represented in FIG. 4. For example, a clinical target volume contour 404, a planning target volume contour 406, and a chest wall contour 408 are each illustrated. The seed grid 402 is centered at the isocenter 410. Each image slice that has been resliced may include a seed grid 402. Including a seed grid 402 at each possible image slice allows for a treatment plan to be accurately planned at different depth levels of a target volume.

The seed grid 402 of FIG. 4 may correspond to a physical template used by a medical practitioner during a radiation treatment procedure. Each insertion point 412 on the seed grid 402 may represent a location for a seed needle during the radiation therapy procedure. Thus, providing a seed grid 402 on a medical image slice that corresponds to a physical seed template allows a medical practitioner to have a virtual guide to each needle insertion point. The efficiency and accuracy of a seed treatment procedure is improved because the system 100 of FIG. 1 has the capability to formulate a treatment plan for the specific seed template chosen for the procedure.

Figure 5:
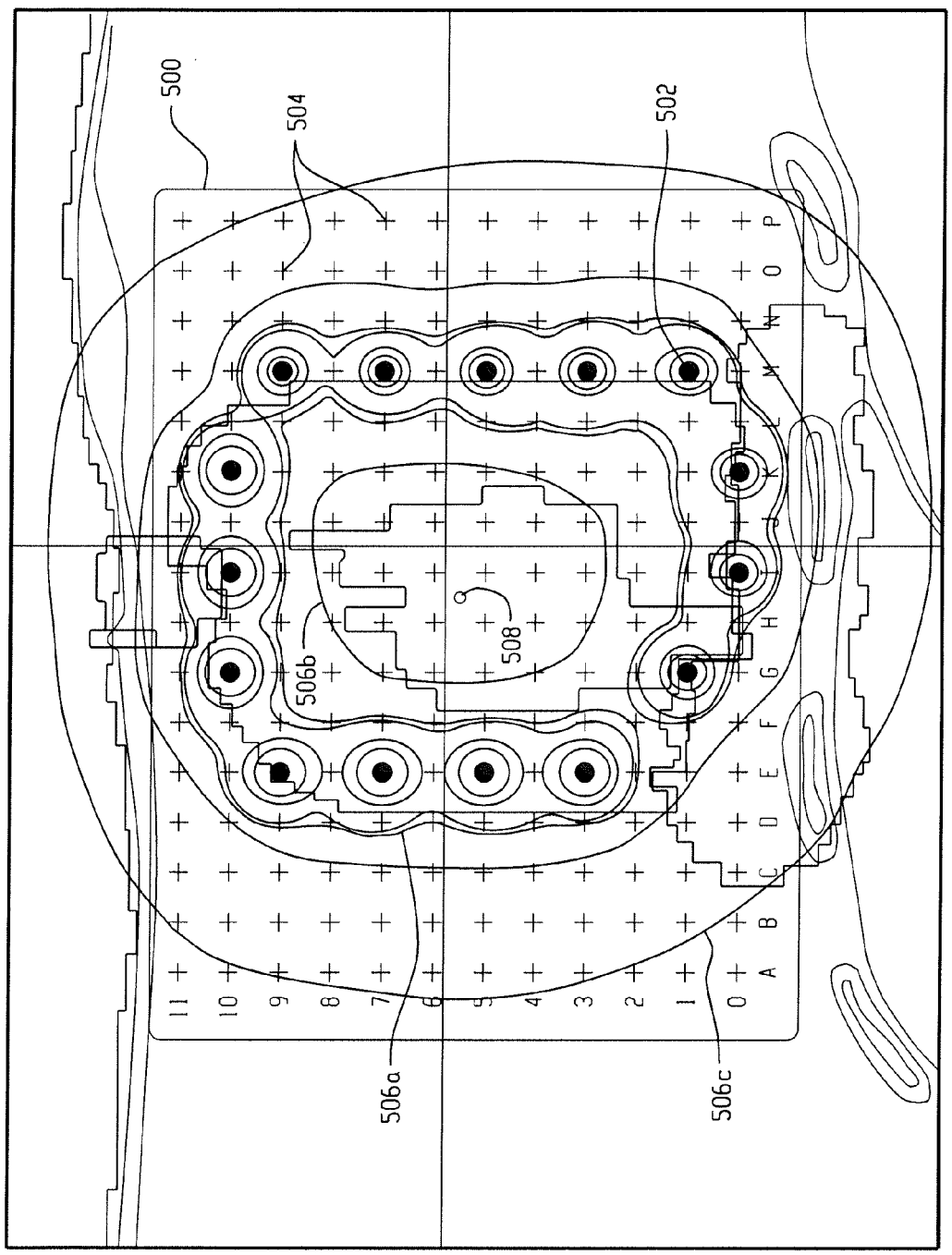

Referring back to FIG. 1, after a seed grid template is selected at the seed grid generator 106, the seed plan generator 108 creates a treatment plan comprising treatment plan data 110. A treatment plan includes at least the contour image data on a resliced image, a seed grid template, seed grid position 122, and dosing plan 124. With reference to FIG. 5, the seed plan generator 108 of FIG. 1, configures a treatment plan including seeds 502 on selected insertion points 504 of the seed grid 500. Each seed 502 may be placed at any of the insertion points 504. When a seed 502 is placed on the seed grid 500, dose level markers 506*a-c* indicate the approximate area that will receive treatment. Any number or combination of dose level markers 506*a-c* may be used to indicate different dose levels for a treatment plan. If a seed 502 is added or removed from the seed grid 500, the seed plan generator may be configured to automatically adjust the dose level markers 506*a-c* to indicate the new plan of treatment. Similarly, FIG. 5 illustrates only one depth, or one resliced image. If a radiation treatment plan uses, for example, seeds at varying lengths on a needle, a seed may appear at one insertion point 504 on a resliced image at 5 mm depth, but not appear on a resliced image at 10 mm depth. Therefore, the dose level markers 506*a-c* may be automatically adjusted for each resliced image.

Figure 6:
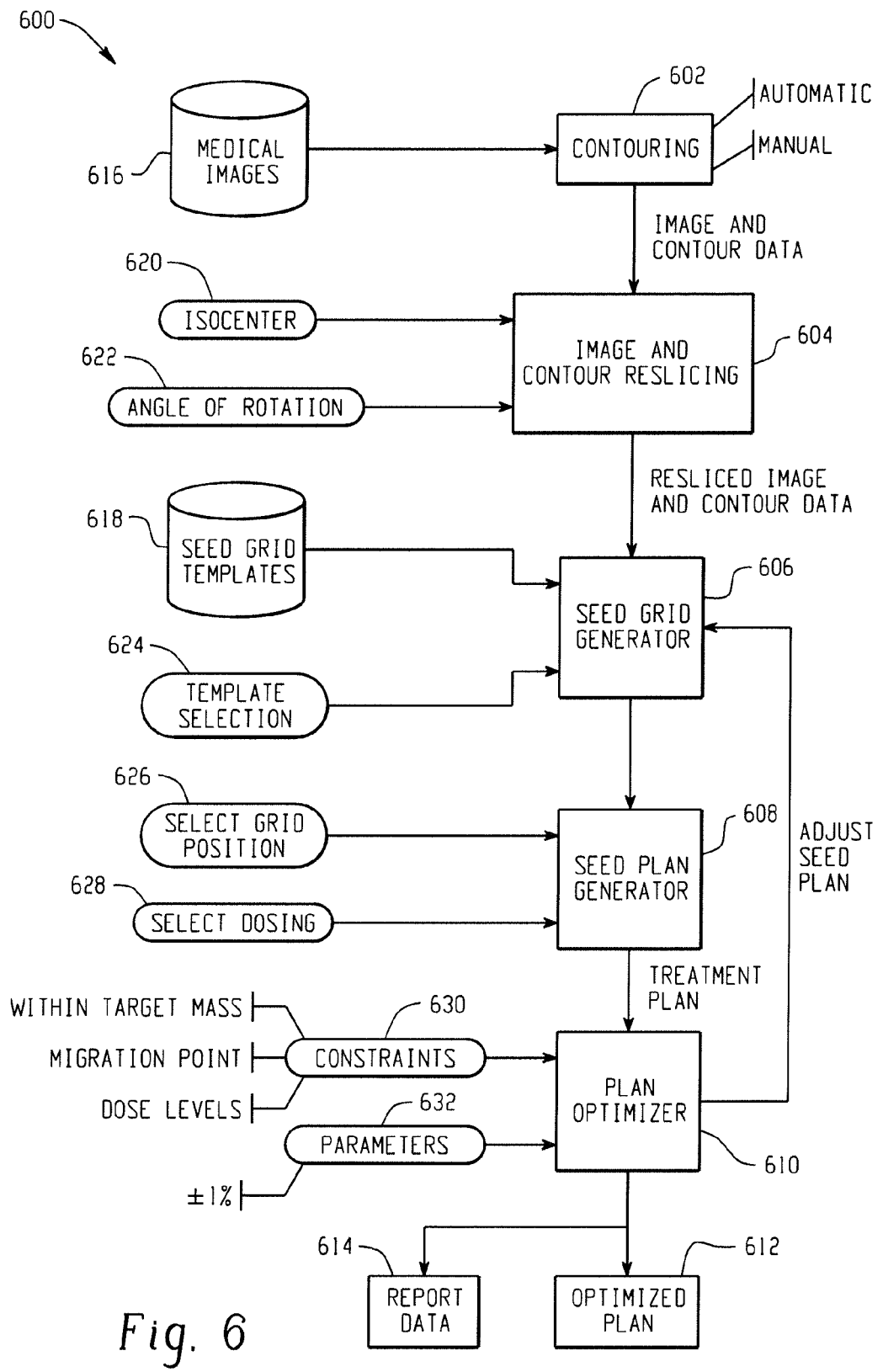

FIG. 6 depicts a block diagram of an example system 600 for reslicing a set of medical images and optimizing a plan of treatment. The system 600 includes a contouring block 602, an image and contour reslicing block 604, a seed grid generator 606, a seed plan generator 608, a plan optimizer 610, an optimized plan 612, and report data 614. Also included in the example system 600 are a medical image database 616 for storing a set of two-dimensional image slices, a seed grid template database 618 for storing seed grid template data, and inputs 620-632. The contouring block 602, image and contour reslicing block 604, seed grid generator 606, seed plan generator 608, medical images database 616, and seed grid template database 618 operate as described above with reference to FIGS. 1-5. In addition to these components, the system 600 of FIG. 6 includes plan optimizer 610. The plan optimizer 610 receives the treatment plan data from the seed plan generator 608. The plan optimizer also receives a set of constraints 630 and a set of parameters 632 and may utilize these inputs to determine if the treatment plan data is optimized.

To determine whether the treatment plan is optimized, the plan optimizer 610, compares the treatment plan data to the one or more constraints 630 and parameters 632 to determine if the treatment plan data is within a required parameter error margin of the constraints 630. The plan optimizer 610 may utilize any method of optimization known to those skilled in the art to perform the comparison. Any number of constraints 630 may be used and FIG. 6, for example, includes needle count or position, seed count or relative position, seed migration or displacement models, and dosage to contours as constraints. The plan optimizer may be configured to compare the treatment plan data, which includes the seed locations, dosage level indicators, and seed grid for each image slice, to the selected constraints 630.

Figure 7:
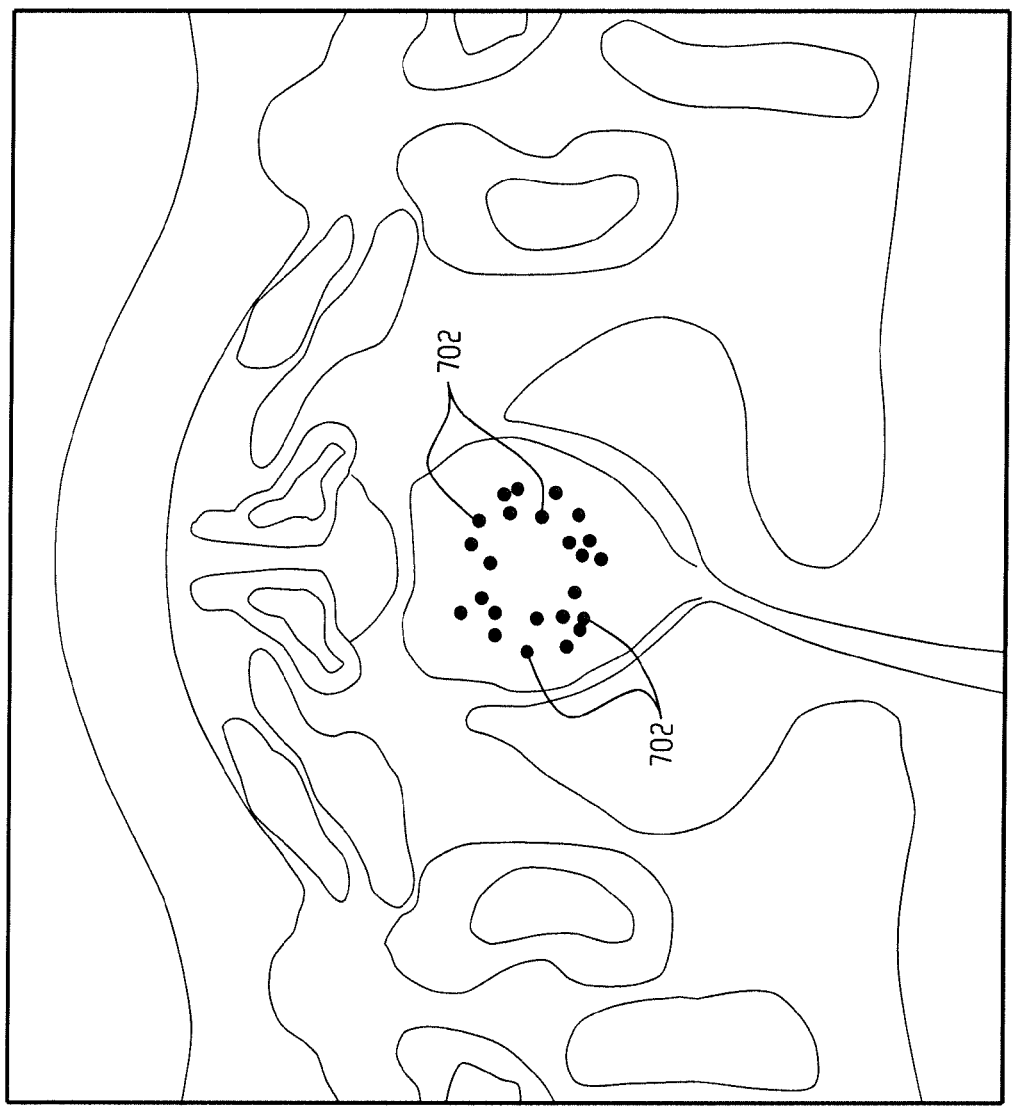
FIG. 7 depicts an example plan verification image displaying seed migration.

If the plan optimizer 610 chooses to compare seed migration data, it may utilize data from a medical image such as the one shown in FIG. 7. FIG. 7 represents medical image data at a point in time during or after a radiation treatment procedure has been performed. The example illustrated in FIG. 7 shows the location of seeds 702 following a radiation seed therapy procedure. The location of the seeds 702 may be compared with the location of a seed in FIG. 5. Because seeds may displace during or migrate following insertion, this comparison is useful to predict where a seed may migrate so that it stays within the target treatment area. If the current seed locations indicated in a treatment plan would allow the target volume to be underdosed or surrounding tissues to be overdosed because of likely seed displacements and migrations, the plan optimizer 610 of FIG. 6 may automatically correct the seed locations to a better seed insertion point. Likewise, the plan optimizer 610, may return the system to the seed grid generator 606 to perform the seed and dose procedure again.

As described above, the medical image data illustrated in FIG. 7 may, for example, be a post-implant verification image. In order to obtain the image data shown in FIG. 7, it may be advantageous to reslice the post-implant image prior to seed identification on the verification image if the seeds were placed at an angle to the imaging slices. This is analogous to the example described above with reference to FIG. 1, except there is no seed grid or template. In this way, the seeds may be identified/placed freely in the image.

Figure 8:
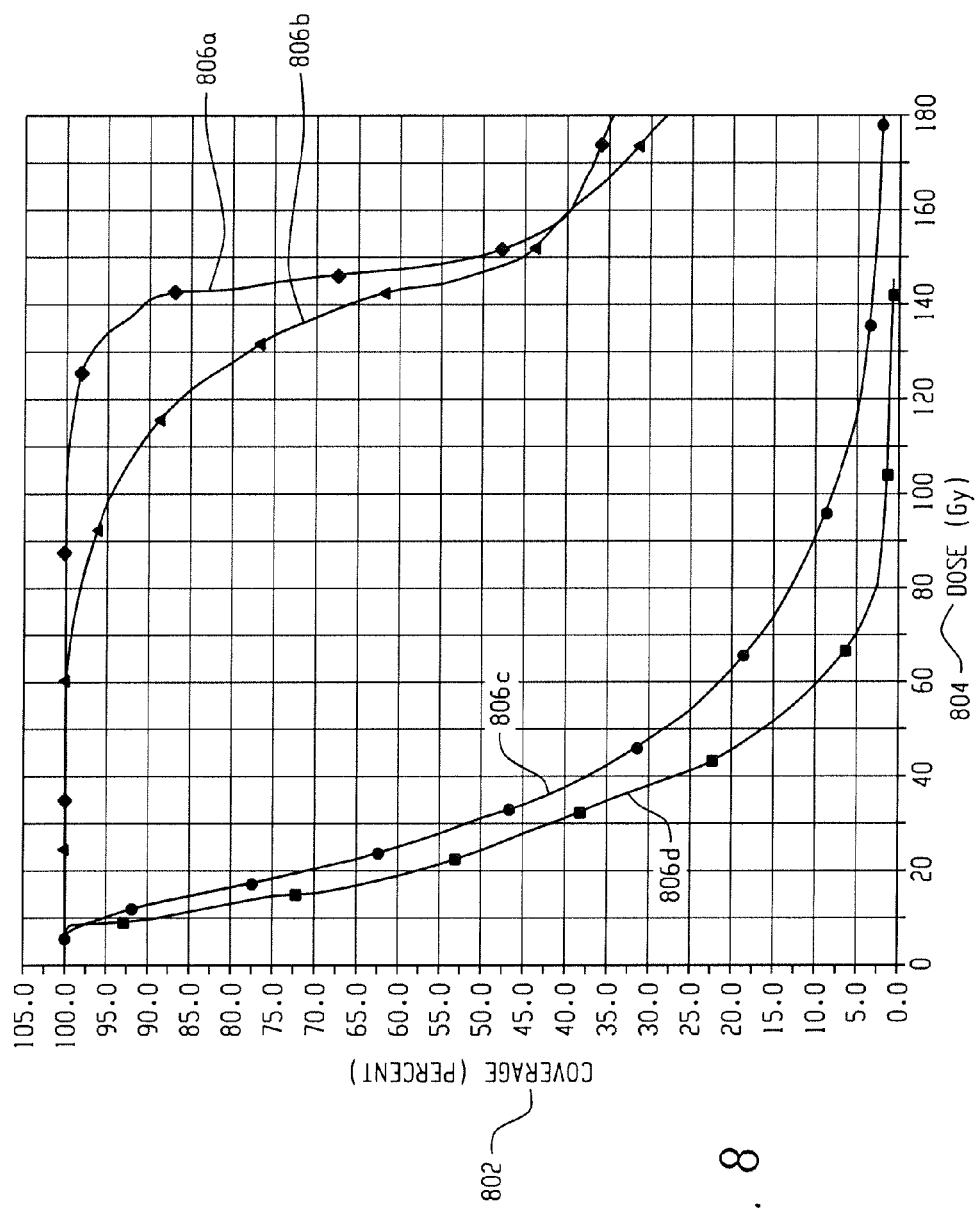
FIG. 8 depicts an example dose volume histogram chart comparing dosage levels in a target treatment area.

Along with the optimization process, the plan optimizer of FIG. 6 may produce report data 614. The report data 614 may include any combination of statistics, operating parameters, image slices, and graphs. For example, shown in FIG. 8 is an example dose volume histogram output graph comparing the conformance of the dose levels in the treatment plan to the target mass. The graph compares the percent coverage 802 of a contour area to the dose level 804 in the selected area. FIG. 8 will be discussed in conjunction with FIG. 4 as a reference. For instance, line 806*a* represents the dose level in a target mass contour 404, line 806*b* represents the dose level in a treatment area contour 406, line 806*c* represents the dose level in a chest wall contour 408, and line 806*d* represents the dose level occurring outside of all contour areas. As shown in the graph of FIG. 8, the highest dosage level should appear in the target mass contour 404 and the lowest dosage level should appear outside of all contour areas. The results of the graph in FIG. 8 may be included in the report data 614 of FIG. 6 so that a seed treatment plan may be manually optimized to ensure the most effective treatment.

With reference again to FIG. 6, if the treatment plan data aligns with the selected constraints within the parameter margin, then the plan optimizer 610 may output report data 614 and an optimized plan 612. If the treatment plan data falls outside of the selected parameter margins to the constraints 630, then the system 600 is configured to adjust the seed plan. The system 600 may be configured to either automatically adjust the seed plan based on the plan optimizer 610, or may be manually adjusted based on the report data 614.

Regardless of either method of adjustment, the seed plan is adjusted by returning to the seed grid generator 606, where a new seed grid may be selected 624 from the seed grid template database 618. As described above with reference to FIG. 1, the seed plan generator 608 generates a treatment plan according to the seed grid position 626 and the dosage 628. This treatment is received by the plan optimizer 610 to perform the optimization techniques described above. When a treatment plan is optimal, the plan optimizer 610 outputs report data 614 and an optimized plan 612.

Figure 9:
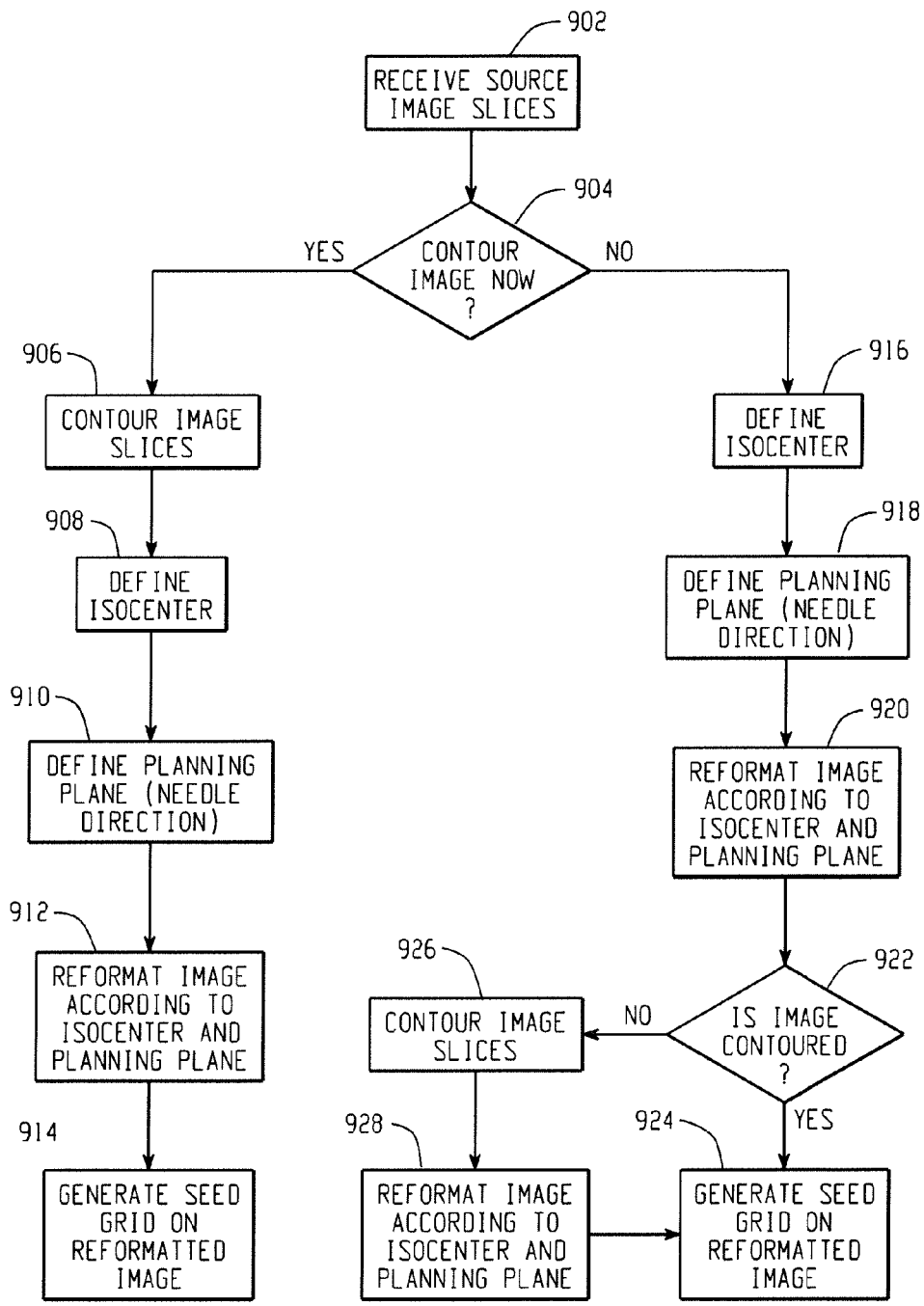
FIG. 9-12 depict flow diagrams of example methods for reslicing a set of medical images.

FIG. 9 is a flow diagram depicting an example method of reslicing a set of medical images. At step 902, source image slices are received. In this example, the image slices are 2D representations of a medical image and have no contouring. At step 904, the method determines whether the image slices will be contoured prior to reslicing. If the image slices are to be contoured prior to reslicing, the method moves to step 906 and contours the image slices. After contouring the image slices an isocenter is defined at step 908 and the planning plane, or the angle of rotation and needle direction, is defined at step 910. At step 912 the contoured image slices are rotated and resliced according to the planning plane defined at step 910. With these resliced images, the method is configured to generate a seed grid on the resliced and contoured images.

If, at step 904, the image slices are not selected for contouring, the method moves to step 916 to define an isocenter. Then, at step 918, a planning plane is defined and utilized at step 920 to rotate and reslice the image slices. At step 922, the method determines whether the image slices have been contoured. If the resliced image slices have been contoured, a seed grid may be generated on the resliced contoured images at step 924. If the resliced images have not been contoured, however, the method goes to step 926 for contouring. Even though the original image slices have already been resliced, the method again reformats the image slices so that the contouring is applied to each resliced image slice at step 928. In another example, step 928 may be omitted, and instead the user may contour the resliced images with no need for further reslicing. In either case, the contoured image slices are then used at step 924 where a seed grid may be generated on each resliced contoured image.

It should be understood that similar to the other processing flows described herein, one or more of the steps and the order in the flowchart may be altered, deleted, modified and/or augmented and still achieve the desired outcome.

Figure 10:
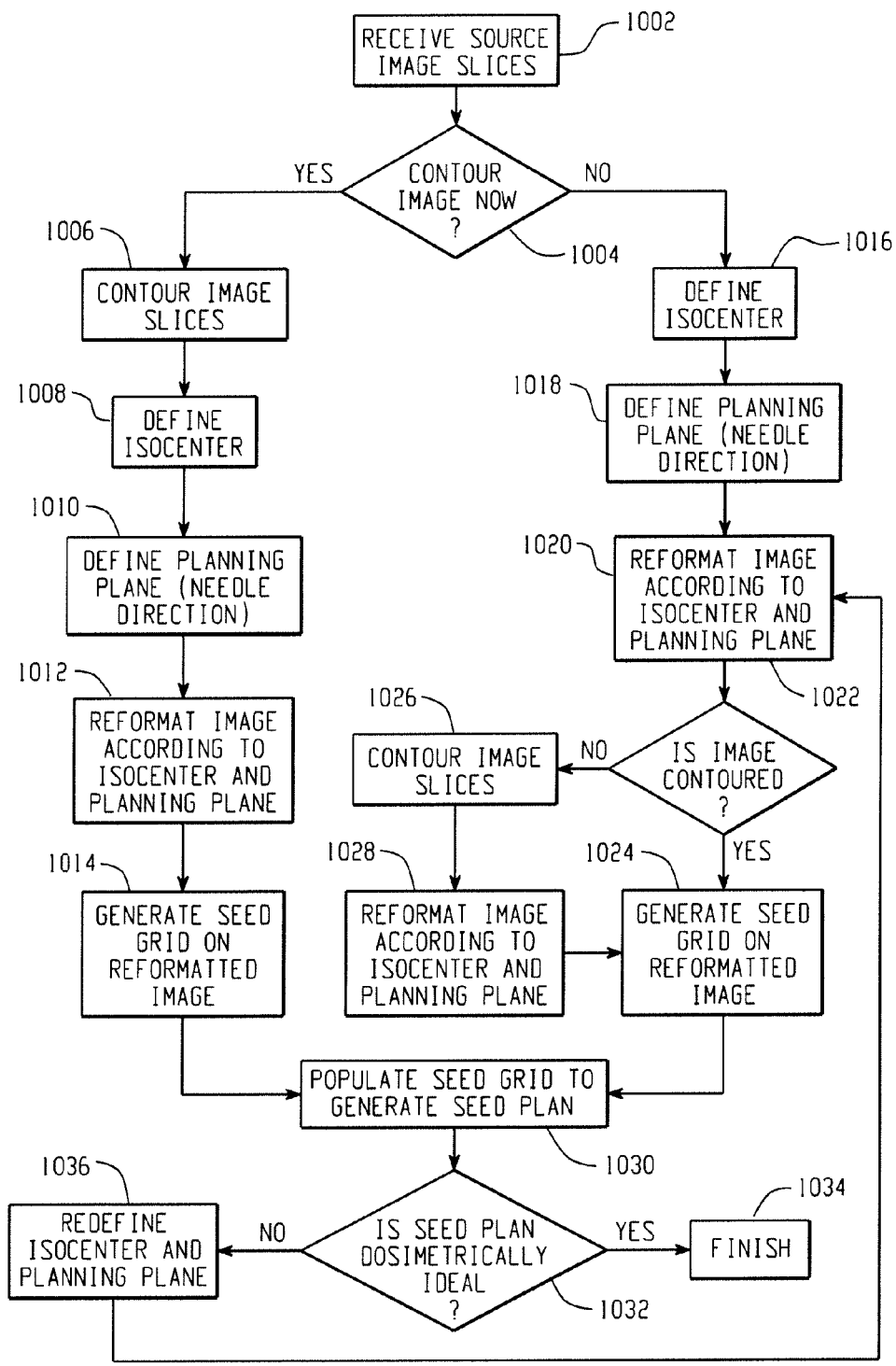

FIG. 10 is a flow diagram depicting an example method of reslicing a set of medical images and determining whether a seed plan is optimal. At step 1002, source image slices are received. In this example, the image slices are 2D representations of a medical image and have no contouring. At step 1004, the method determines whether the image slices will be contoured prior to reslicing. If the image slices are to be contoured prior to reslicing, the method moves to step 1006 and contours the image slices. After contouring the image slices an isocenter is defined at step 1008 and the planning plane, or the angle of rotation and needle direction, is defined at step 1010. At step 1012 the contoured image slices are rotated and resliced according to the planning plane defined at step 1010. With these resliced images, the method is configured to generate a seed grid on the resliced and contoured images.

If, at step 1004, the image slices are not selected for contouring, the method moves to step 1016 to define an isocenter. Then, at step 1018, a planning plane is defined and utilized at step 1020 to rotate and reslice the image slices. At step 1022, the method determines whether the image slices have been contoured. If the resliced image slices have been contoured, a seed grid may be generated on the resliced contoured images at step 1024. If the resliced images have not been contoured, however, the method goes to step 1026 for contouring. Even though the original image slices have already been resliced, the method again reformats the image slices so that the contouring is applied to each resliced image slice at step 1028. In another example, step 1028 may be omitted, and instead the user may contour the resliced images with no need for further reslicing. In either case, the contoured image slices are then used at step 1024 where a seed grid may be generated on each resliced contoured image.

After steps 1014 or 1024 the method moves to step 1030 to populate the seed grid and generate a seed plan. At step 1030, the seed grid may be populated with seeds at different insertion points as described above with reference to FIGS. 1 and 5. Following the creation of the seed plan, step 1032 determines whether the seed plan is dosimetrically ideal. This process may be accomplished through any number of comparison methods. One example is the utilization of the graph of FIG. 8 to determine the percentage of a dose level at different contour areas. If the method determines at step 1032 that an insufficient percentage of the target area is receiving the prescription dose or the dose is imbalanced around the target, then it moves to step 1036 where the isocenter and planning plane may be redefined. Redefining the isocenter and planning plane may provide for a better reslicing of the image slices so that a more accurate seed plan may be generated. After step 1036, the method returns to step 1020 and the process is repeated as necessary until the dose plan is dosimetrically ideal and the method may finish at step 1034.

Figure 11:
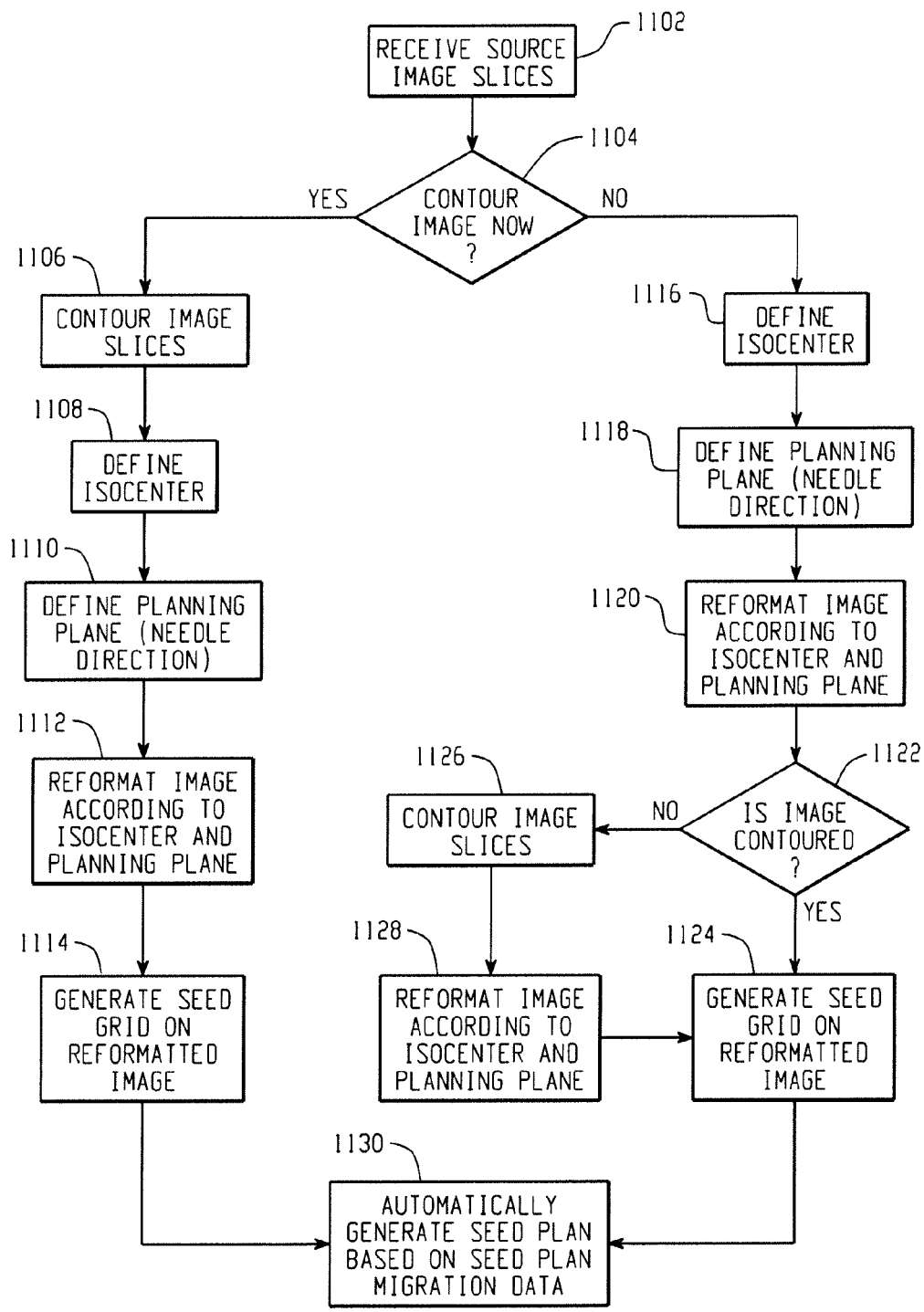

FIG. 11 is a flow diagram depicting an example method of reslicing a set of medical images to automatically generate a seed plan based on seed migration data. At step 1102, source image slices are received. In this example, the image slices are 2D representations of a medical image and have no contouring. At step 1104, the method determines whether the image slices will be contoured prior to reslicing. If the image slices are to be contoured prior to reslicing, the method moves to step 1106 and contours the image slices. After contouring the image slices an isocenter is defined at step 1108 and the planning plane, or the angle of rotation and needle direction, is defined at step 1110. At step 1112 the contoured image slices are rotated and resliced according the planning plane defined at step 1110. With these resliced images, the method is configured to generate a seed grid on the resliced and contoured images.

If, at step 1104, the image slices are not selected for contouring, the method moves to step 1116 to define an isocenter. Then, at step 1118, a planning plane is defined and utilized at step 1120 to rotate and reslice the image slices. At step 1122, the method determines whether the image slices have been contoured. If the resliced image slices have been contoured, a seed grid may be generated on the resliced contoured images at step 1124. If the resliced images have not been contoured, however, the method goes to step 1126 for contouring. Even though the original image slices have already been resliced, the method again reformats the image slices so that the contouring is applied to each resliced image slice at step 1128. These resliced contoured image slices are then used at step 1124 where a seed grid may be generated on each resliced contoured image.

After steps 1114 or 1124 the method moves to step 1130 to automatically generate a seed plan based on seed migration data. At step 1130, the method receives seed plan deflection and migration data from one or more databases. The seed plan migration data includes information related to the planned implant location or initial implant location of a seed and data related to the location of a seed at a point in time after the initial implant procedure. This data allows for a determination of an optimal implant location based on how seeds may migrate from the initial or planned implant location. The method then generates an optimal seed plan accounting for any possible migration of each seed.

The seed migration data may require a method of identifying corresponding seeds in the treatment plan with seeds in a post-implant verification image, for example as shown in FIG. 7. The method for correlating seeds may include a seed registration algorithm which seeks to minimize differences in the relative position of the seeds when comparing the seed plan to the post-implant verification image. The seed migration data could be used, for example, to generate a seed migration model which defines the likelihood that each seed will deflect or migrate from the planned implant location. This model can then be used to describe the likely dosimetric outcome of a medical practitioner attempting to place a seed at a given location.

Figure 12:
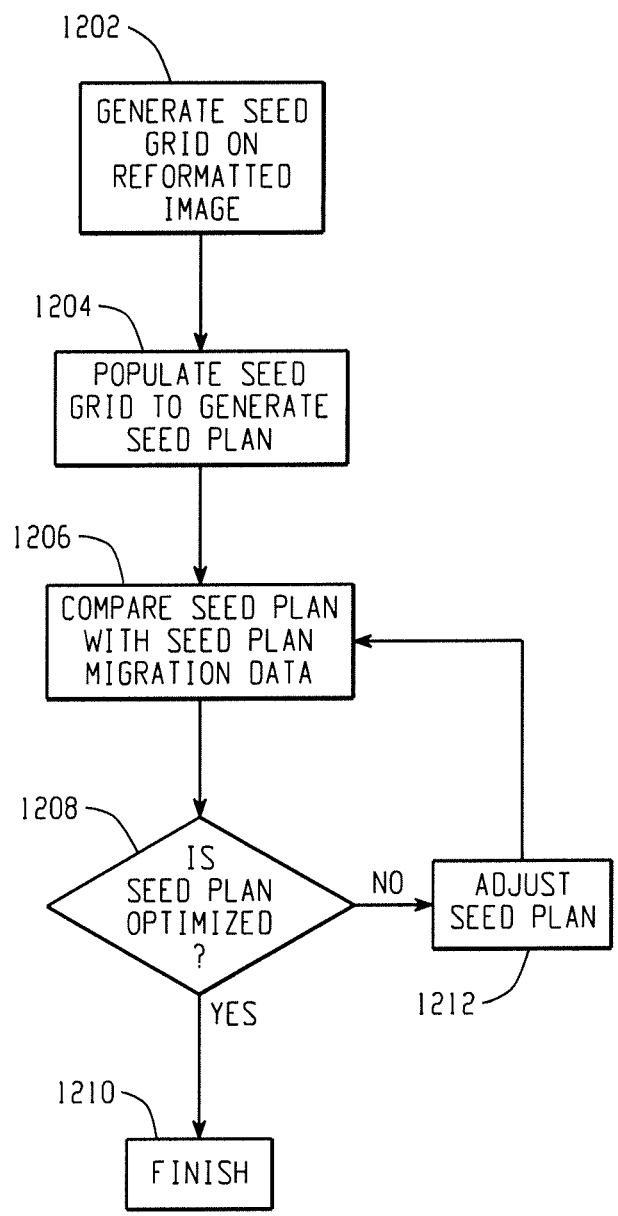

FIG. 12 is another example flow diagram depicting an example method of reslicing a set of medical images to generate a seed plan based on seed migration data. The method of FIG. 12 begins at step 1202 where a seed grid has been generated on an image, possibly a resliced and reformatted image. At step 1204, the seed grid is populated with the dose plan and a seed plan is generated. This generated seed plan is then compared, at step 1206, with seed plan migration data. A comparison between the generated seed plan and the seed plan migration data occurs at step 1208. A predefined set of constraints and parameters allows the method to determine whether the generated seed plan is optimized based on how the seeds may migrate after implantation. If the method determines that the generated seed plan is optimized, then the seed plan is outputted at step 1210. This seed plan may include data which indicates the range of likely delivery outcomes of the plan given the seed migration model. For example, a dose volume histogram graph may include error bars indicating the range of likely dose levels for each possible output. If, however, the generated seed plan is not optimized based on the seed plan migration data, the seed plan is adjusted at step 1212. The process at steps 1206 and 1208 is then repeated until the seed plan is optimized based on the seed plan migration data.

Figure 13:
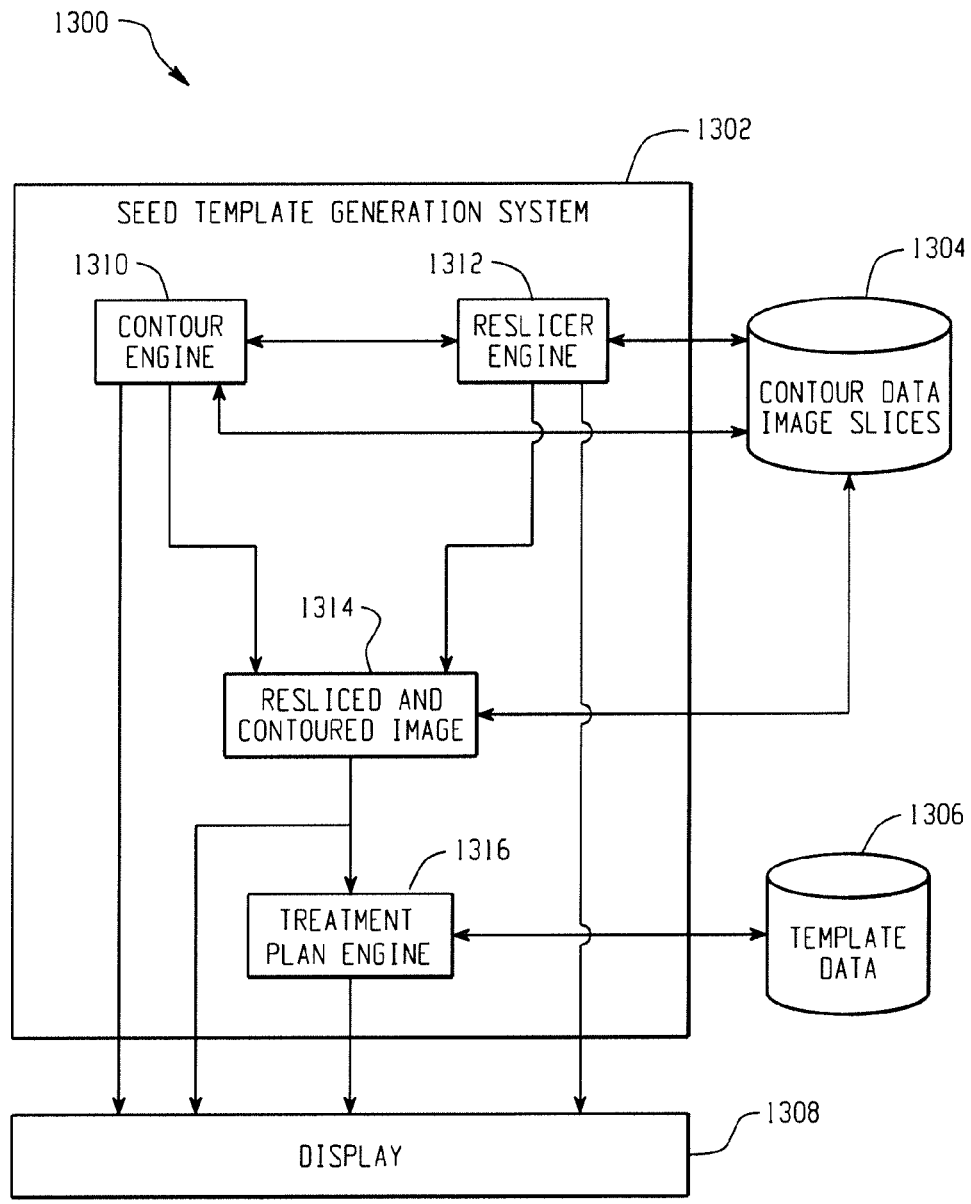
FIG. 13 depicts an example system for reslicing medical images.

FIG. 13 depicts a block diagram of an example system 1300 for reslicing a set of medical images to generate a seed plan. The system includes a seed template generation system 1302, a contour data and image slices database 1304, a template data database 1306, and a display 1308. The seed template generation system further includes a contour engine 1310, a reslicer engine 1312, resliced and contoured image 1314, and a treatment plan engine 1316.

In operation, a set of medical image slices from the contour data and image slices database 1304 are loaded onto the reslicer engine 1312 or the contour engine 1310. The contour engine 1310 is configured to contour a set of medical image slices. The contours may include, for example, a clinical target volume contour' 202, a planning target volume contour 204, and a chest wall contour 206, as illustrated in FIG. 2. The reslicer engine 1312 is configured to define an isocenter and angle of rotation to reslice the image slices. This process may occur either before or after the image slices are contoured by the contour engine 1310. Once an isocenter and angle of rotation are defined, the reslicer engine is further configured to rotate and reformat the image slices along the angle of rotation. The output of the process is the resliced and contoured image 1314.

The treatment plan engine 1316 receives the resliced and contoured image 1314 and may perform a number of operations related to the placement and selection of a seed grid. The treatment plan engine 1316 receives a seed grid template from the template data database 1306. Once a seed grid template is selected, the seed grid engine formats the resliced image slices with the selected grid. The treatment plan engine 1316 may also be further configured to utilize the selected grid to produce a seed treatment plan, as described in detail above with reference to FIGS. 1 and 5.

Instead of producing a seed grid template on a resliced image, the treatment plan engine 1316 may be configured to produce a treatment plan for use in an external beam radiation therapy. For such a treatment, treatment beams are used by the medical practitioner for the radiation therapy. In a procedure using treatment beams, the resliced images may still be utilized, however, a seed grid and physical template corresponding to the seed grid template is not utilized. The treatment plan engine 1316 may also incorporate a plan optimizer which makes use of the model correlating the original plan with the verification images.

Figure 14:
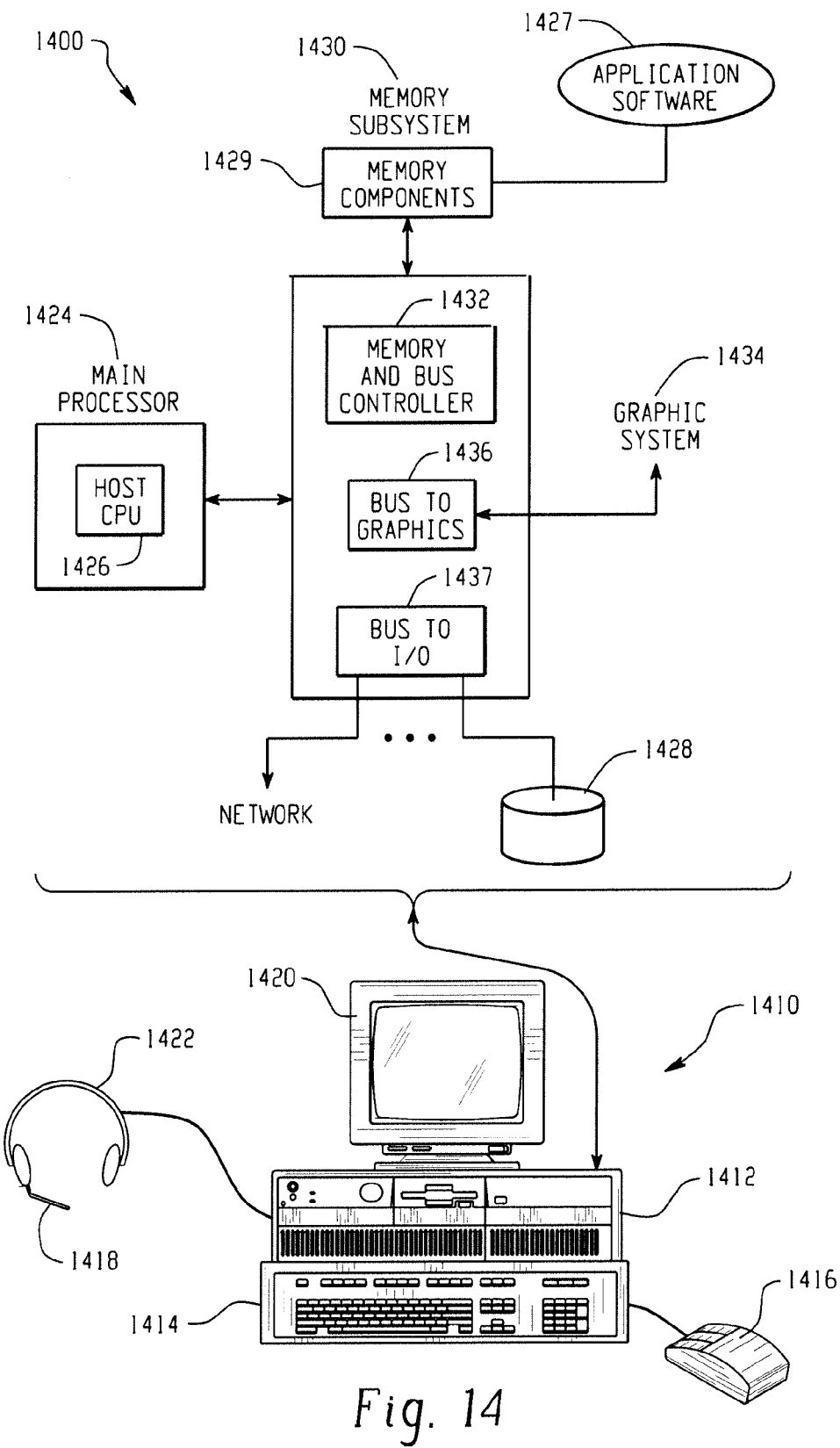
FIG. 14 is a block diagram of hardware which may be used to implement the various embodiments described herein.

FIG. 14 is a block diagram of hardware 1410 which may be used to implement the various embodiments described herein. The hardware 1410 may be a personal computer system or server system that includes a computer having as input devices keyboard 1414, mouse 1416, and microphone 1418. Output devices such as a monitor 1420 and speakers 1422 may also be provided. The reader will recognize that other types of input and output devices may be provided and that the present invention is not limited by the particular hardware configuration.

Residing within computer 1420 is a main processor 1424 which is comprised of a host central processing unit 1426 (CPU). Software applications 1427 may be loaded from, for example, disk 1428 (or other device), into main memory 1429 from which the software application 1427 may be run on the host CPU 1426. The main processor 1424 operates in conjunction with a memory subsystem 1430. The memory subsystem 1430 is comprised of the main memory 1429, which may be comprised of a number of memory components, and a memory and bus controller 1432 which operates to control access to the main memory 1429. The main memory 1429 and controller 1432 may be in communication with a graphics system 1434 through a bus 1436. Other buses may exist, such as a PCI bus 1437, which interfaces to I/O devices or storage devices, such as disk 1428 or a CDROM, or to provide network access.

This written description uses examples to disclose the invention, including the best mode, and also to enable a person skilled in the art to make and use the invention. The patentable scope of the invention may include other examples that occur to those skilled in the art.

For instance, the systems and methods described herein, such as the method of relating treatment plans to delivered treatments based in verification images, can be applied to brachytherapy seed plans as well as other areas, such as external beam radiation therapy (EBRT). In the case of EBRT, the verification image may come from an imaging system directly related to the treatment room. For example, a cone-beam CT may be attached to the linear accelerator in the treatment room. The verification image can then be related to the original treatment plan using any model or image registration technique, such as deformable image registration, in order to develop a model for treatment delivery uncertainty analogous to a seed migration model. More specifically, deformable registration could be used to correlate each voxel in the planning image with the corresponding anatomy in a set of verification images. With dose calculation performed on the verification images, each voxel in the planning image would have a planned dose and a delivered dose. A patient-specific or population-based model could be trained with a set of the correlated planned and verification doses which would describe the likely variation in actual dose delivered for each voxel in a patient's anatomy. To develop a population-based model, the voxel-level positional or dose variations could be related to one another by deformable registration to a common atlas, which could then be registered to a patient planning image. This model could then be used for plan optimization for future treatment fractions for the same patient or for optimization of treatment plans for other patients.

It is further noted that the systems and methods described herein may be implemented on various types of computer architectures, such as for example on a single general purpose computer or workstation, or on a networked system, or in a client-server configuration, or in an application service provider configuration.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform methods described herein. Other implementations may also be used, however, such as firmware or even appropriately designed hardware configured to carry out the methods and systems described herein.

The systems' and methods' data may be stored and implemented in one or more different types of computer-implemented ways, such as different types of storage devices and programming constructs (e.g., data stores, RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, etc.) that contain instructions for use in execution by a processor to perform the methods' operations and implement the systems described herein.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

What is claimed is:

1. A processor-implemented method for generating a seed grid for use in radiation therapy, comprising:
   receiving one or more image slices, the image slices comprising one or more cross sectional medical images;
   contouring each image slice to generate target contour data to identify one or more objects within each image slice;
   defining an isocenter and an angle of rotation of the image slices;
   rotating the contoured image slices about the angle of rotation to produce a resliced contoured image, the resliced contoured image being the image slice rotated at an angle perpendicular to the angle of rotation; and
   generating a seed grid perpendicular to the angle of rotation, the seed grid comprising indicators for a seed plan, the indicators for the seed plan comprising locations for insertion points for radiation containing seeds for use in radiation therapy.

2. The method of claim 1, further comprising:
   adjusting the seed grid location; and
   defining a new isocenter and new angle of rotation based on the adjusted seed grid and repeating the rotating and generating steps to produce a resliced contoured image with the seed grid perpendicular to the new angle of rotation and centered at the new isocenter.

3. The method of claim 1, further comprising:
   inserting seeds at one or more indicators on the seed grid to generate a seed plan;
   determining whether the seed plan is optimized by,
   receiving seed plan migration data;
   comparing the seed plan migration data to the seed plan with predetermined indicators to generate an optimized seed plan.

4. The method of claim 1, wherein the isocenter defines a center point of a target volume.

5. The method of claim 1, wherein the angle of rotation is a needle path.

6. The method of claim 5, wherein the needle path is configured for a fiducial needle.

7. The method of claim 1, wherein the locations of the insertion points represent insertion points for seed-carrying needles.

8. The method of claim 7, wherein the seed-carrying needles comprise one or more seeds distributed along the length of the needle shaft.

9. The method of claim 8, wherein the one or more seeds are distributed along the length of the needle shaft so as to provide a deposit of a seed at varying depths of a target volume.

10. The method of claim 1, wherein the angle of rotation is in plane with beams for use in external radiation therapy.

11. A system for generating a seed grid for use in radiation therapy, the system comprising:
    an image database, the image database comprising image slices, the image slices comprising one or more cross sectional medical images;
    a seed template database, the seed grid database comprising one or more seed templates, the seed template comprising indicators for a seed plan, the indicators for the seed plan comprising locations for radiation containing seeds for the radiation therapy;
    a contour engine, the contour engine configured to generate target contour data to identify one or more objects within each image slice;
    a reslicer engine configured to rotate the contoured image about an angle of rotation to produce a resliced contoured image, the resliced contoured image being the image slice rotated at an angle perpendicular to the angle of rotation and intersecting an isocenter; and
    a seed grid engine, the seed grid engine configured to generate a seed grid perpendicular to the angle of rotation, the seed grid corresponding to a seed template from the seed template database, wherein the contour engine, reslicer engine, and seed grid engine comprise software instructions stored in one or more memory devices and executable by one or more processors.

12. The system of claim 11, wherein the seed grid engine is further configured to:
   adjust the seed grid location; and
   the reslicer engine is further configured to define a new isocenter and new angle of rotation based on the adjusted seed grid to produce a resliced contoured image with the adjusted seed grid perpendicular to the new angle of rotation and centered at the new isocenter.

13. The system of claim 11, further comprising a seed plan engine, the seed plan engine configured to insert seeds at one or more indicators on the seed grid to generate a seed plan,
   wherein the seed plan engine comprise software instructions stored in one or more memory devices and executable by one or more processors.

14. The system of claim 13, further comprising a plan optimizer engine, the plan optimizer engine configured to determine whether the seed plan is optimized by receiving seed plan migration data and comparing the seed plan migration data to the seed plan with predetermined indicators to generate an optimized seed plan,
   wherein the plan optimizer engine comprises software instructions stored in one or more memory devices and executable by one or more processors.

15. The system of claim 11, wherein the isocenter defines a center point of a target mass.

16. The system of claim 11, wherein the angle of rotation is a needle path.

17. The system of claim 16, wherein the needle path is configured for a fiducial needle.

18. The system of claim 11, wherein the locations for radiation containing seeds represent insertion points for seed-carrying needles.

19. The system of claim 18, wherein the seed-carrying needles comprise one or more seeds distributed along the length of the needle shaft.

20. The system of claim 19, wherein the one or more seeds are distributed along the length of the needle shaft so as to provide a deposit of a seed at varying depths of a target volume.

21. A processor implemented method for reformatting medical image slices, comprising:
   receiving one or more image slices, the image slices comprising one or more cross sectional medical images;
   contouring each image slice to generate target contour data to identify one or more objects within each image slice;
   defining an isocenter and an angle of the image slices, the isocenter defining a center point of a target mass and the angle defining a treatment plane;
   rotating the contoured image slices about the angle to produce a resliced contoured image, the resliced contoured image being the image slice rotated at an angle perpendicular to the needle angle.

22. The method of claim 21, wherein the resliced contoured image is for use in identifying locations for radiation containing seeds for the radiation therapy.

23. The method of claim 21, wherein the resliced contoured image is for use in external beam radiation therapy.

* * * * *